United States Patent [19]
Daniel

[11] Patent Number: 5,269,799
[45] Date of Patent: Dec. 14, 1993

[54] FINGER PRICKER

[76] Inventor: Richard F. Daniel, Rte. 2, Box 305, Shannon, Miss. 38868

[21] Appl. No.: 972,218

[22] Filed: Nov. 5, 1992

[51] Int. Cl.⁵ .......................................... A61B 17/34
[52] U.S. Cl. ................................................. 606/182
[58] Field of Search ............... 128/760, 763; 606/181, 606/182

[56]                References Cited
          U.S. PATENT DOCUMENTS

| Re. 32,922 | 5/1989 | Levin et al. | 606/182 |
| 4,203,446 | 5/1980 | Höfert et al. | 606/182 |
| 4,379,456 | 4/1983 | Cornell et al. | 606/182 |
| 4,469,110 | 9/1984 | Slama | 606/182 |

*Primary Examiner*—Max Hindenburg
*Attorney, Agent, or Firm*—John E. Vandigriff

[57]                ABSTRACT

The invention is to an apparatus for holding and moving a needle for drawing blood from a finger. The apparatus includes a tubular body for receiving a needle, and a cap, with a needle point opening, for closing one end of the tubular body. First, second and third levers for are used for moving the cap to open the end of the tubular body, for ejecting a needle from the apparatus, and for releasing the needle from a cocked position to push the needle into a finger held against the closed cap.

6 Claims, 2 Drawing Sheets

FINGER PRICKER

FIELD OF THE INVENTION

This invention relates to a needle holder, and more particularly to a needle holder for holding a needle to prick a finger for purposes of drawing blood.

BACKGROUND OF THE INVENTION

In practice, needles used to prick a finger to draw a blood sample for medical purposes are held in the medical technician's hand while pricking a finger to draw blood. This is effective for drawing blood, but this subjects the technician to accidentally sticking of her own finger or another part of the hand or arm. If the accidental pricking is done prior to drawing blood from another person, no great harm results. However, if the technician pricks herself after drawing a blood sample from another person, the technician is subjected any diseases that the other person may have. This is not an acceptable event, particularly in the present time when diseases such as AIDs is becoming more common.

BRIEF SUMMARY OF THE INVENTION

The operation of the invention is as follows. A needle is loaded into a needle holder of the present invention. There is a cover over the tip of the needle to protect the needle end and to prevent accidental pricking with the needle. The needle holder is such that when the needled is loaded into the holder, a cap is open during loading and unloading of the needle. After the needle is loaded, the cap is closed. The needle tip protrudes from a small hole in the cap.

A first lever is pulled back against a spring into a holding notch, holding the cap open. The needle is inserted, and the protective cover over the needle is broken off. A pair of levers that have been pushed forward during the needle load operation are pulled back to a notch holding the needle in a cocked position. The first lever is then pushed forward to close the cap and the spring holds the cap closed.

To prick a finger, the pair of levers are pushed off a holding notch which has been holding th needle in the cocked position. The needle will move forward to prick the finger which is held against the cap over the needle end. The needle is stopped at an idle notch to prevent excessive penetration of the needle.

The needle is ejected by pulling the first lever back, opening the cap, and one of the pair of levers is pushed forward to eject the needle into a waste disposal container. The technician does not have to handle the needle after the protective tip has been removed, and a blood sample taken.

The technical advance represented by the invention as well as the objects thereof will become apparent from the following description of a preferred embodiment of the invention when considered in conjunction with the accompanying drawings, and the novel features set forth in the appended claims.

DESCRIPTION OF A PREFERRED EMBODIMENT

Figure 1:
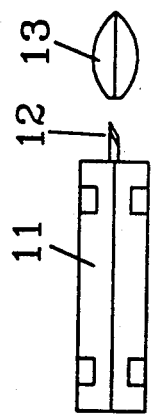
FIG. 1 illustrates a typical needle used in drawing blood.

FIG. 1 illustrates a typical needle use in drawing blood samples. Needle 12 is held in a plastic body 11. End cap 13 is placed over the end of the needle, and removed during use.

Figure 2:
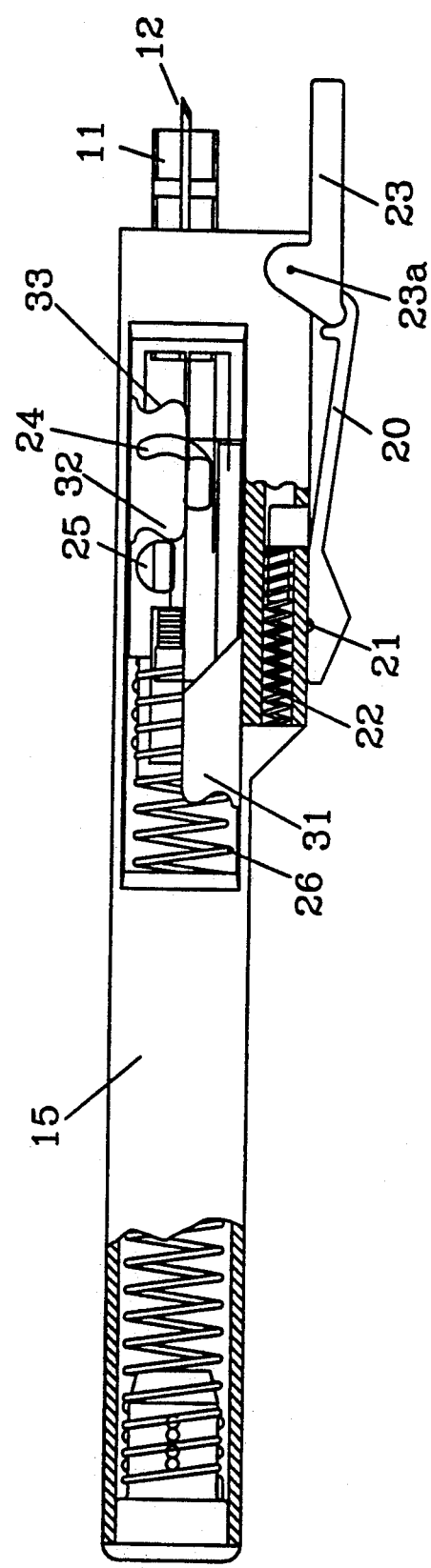
FIG. 2 is side view of the finger pricker at load position.
Figure 3:
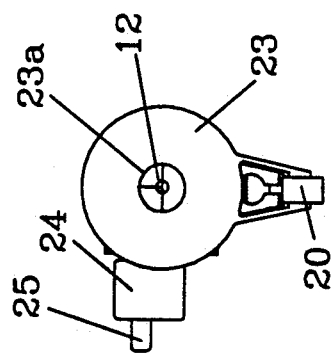
FIG. 3 is an end view of the finger pricker.
Figure 4:
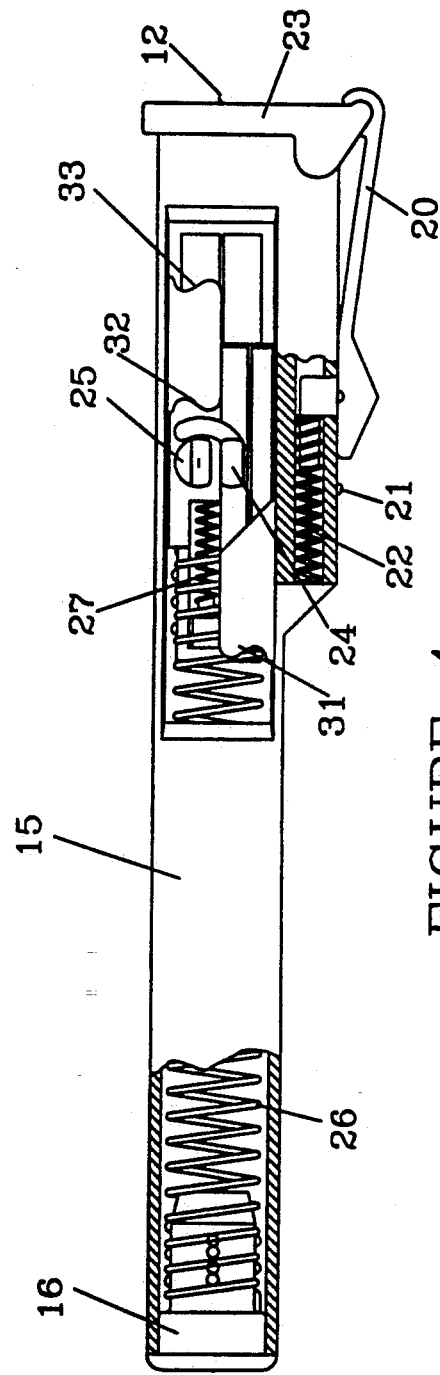
FIG. 4 is a partial view of the finger pricker at ejection position.

FIG. 2 illustrates the finger pricker in the load/unload state, and FIG. 4 illustrates the finger pricker in the load state.

To load the needle, lever 20 is pulled back to notch 21. When pulling lever 20 back, cap 23 pivots about pivot 23a, opening the end of the needle holder. With cap 23 open, the needle is either loaded or ejected.

During the load operation, levers 24 and 25 are rotated downward, as viewed in FIG. 2, and moved forward and then rotated upward into notch 33 while needle holder 11 is being pushed into body 15. Needle cap 13 is then broken off.

Levers 24 and 25 are rotated downward off notch 33 to draw needle holder 11 and needle 12 into body 15 of the finger pricker.

Lever 20 is pushed forward to close cap 23, and is held in place by spring 22.

Levers 24 and 25 are pulled back and rotated downward into holding notch 31. The finger pricker is now ready for use.

End cap 23 with hole 23a, is placed against a finger and levers 24 and 25 are rotated upward off holding notch 31. Spring 26, compressed against end cap 16 during needle loading, moves levers 24 and 25 and needled holder 11 forward, pricking the finger as needle 12 extends out of opening 23a in cap 23. Levers 24 and 25 stop at idle notch 32.

To eject the used needle 12, lever 20 is pulled back to notch 21, opening cap 23. Lever 24 is pushed forward to eject needle holder 11. Spring 27 will pull lever 24 back to the idle position. Lever 20 is then pushed forward to close cap 23.

Through the use of the finger pricker, the needle does not have to be handled after use. The needle is ejected into a disposal container.

What is claimed:

1. An apparatus for holding and moving a needle for drawing blood from a finger, comprising:
   a tubular body for receiving a needle;
   a cap for closing one end of the tubular body;
   a first lever attached to said cap for moving the cap to open the end of the tubular body;
   a second lever, having an idle position and a cocked position, for ejecting a needle from the apparatus; and
   a third lever, having an idle position and a cocked position, for releasing the needle from said cocked position to push the needle into a finger held against the closed cap.

2. The apparatus according to claim 1, including a first spring to hold said first lever in a position to maintain said cap in a closed position.

3. The apparatus according to claim 1, wherein said second lever is attached to a second spring to maintain said second lever in the idle position when said second lever is not ejecting a needle.

4. The apparatus according to claim 1, said second and third levers are movable together to the cocked position to apply pressure against a third spring, said third spring pushing the needle into the finger to draw blood from the finger.

5. An apparatus for holding and moving a needle for drawing blood from a finger, comprising:
- a tubular body for receiving a needle;
- a cap for closing one end of the tubular body;
- a first spring loaded lever attached to said cap for moving the cap to open the end of the tubular body;
- a second lever, having an idle position and a cocked position, for ejecting a needle from the apparatus; and
- a third lever and spring, said third lever having an idle position and a cocked position, for releasing the needle from said cocked position, said spring pushing the needle into a finger held against the closed cap.

6. The apparatus according to claim 5, wherein said second lever is attached to a second spring to maintain said second lever in the idle position when said second lever is not ejecting a needle.

* * * * *